United States Patent [19]

Bornengo et al.

[11] 4,147,697
[45] Apr. 3, 1979

[54] QUATERNARIZATION OF DIPYRIDYL ACETATE TO N,N'-DIMETHYL-4,4'-DIPYRIDYLIUM DIHALIDE IN ACETIC ACID

[75] Inventors: Mario Bornengo, Massa; Sergio Bacciarelli, Ferrara, both of Italy

[73] Assignee: Montedison S.p.A., Milan, Italy

[21] Appl. No.: 868,383

[22] Filed: Jan. 10, 1978

[30] Foreign Application Priority Data

Jan. 12, 1977 [IT] Italy ............................... 19216 A/77

[51] Int. Cl.$^2$ ........................................... C07D 213/22
[52] U.S. Cl. ................................................... 546/258
[58] Field of Search .................................... 260/296 D

[56] References Cited

U.S. PATENT DOCUMENTS 3,864,352  2/1975  Colchester et al. ............. 260/296 D Primary Examiner—Alan L. Rotman
Attorney, Agent, or Firm—Stevens, Davis, Miller & Mosher

[57] ABSTRACT

A process is disclosed for quaternarizing 4,4'-dipyridyl diacetate to N,N'-dimethyl-4,4'-dipyridylium dihalide by reaction with an alkyl halide, preferably a lower alkyl halide such as methyl chloride, the reaction being carried out by:

using acetic acid as solvent for the 4,4'-dipyridyl diacetate in amounts of at least 1:1 by weight in respect of the diacetate subjected to reaction; and heating the reactants at temperatures ranging from 60° to 150° C. and at pressures ranging from 2 to 10 kg/cm$^2$. The acetic acid used as a solvent may be utilized for further quaternarizations of 4,4'-dipyridyl diacetate. Preferably the acetic acid is recycled to the zone of oxidation of diacetyl-tetrahydrodipyridyl, the resulting product being quaternarized in the same recycled acetic acid.

6 Claims, No Drawings

QUATERNARIZATION OF DIPYRIDYL ACETATE TO N,N'-DIMETHYL-4,4'-DIPYRIDYLIUM DIHALIDE IN ACETIC ACID

This invention relates to a method for quaternarizing dipyridyl diacetate to N,N'-dimethyl-4,4'-dipyridylium dihalide.

More particularly, the present invention relates to the quaternarization of dipyridyl diacetate in acetic acid in one step only, with high yields, excellent purity, and with the possibility of using acetic acid for successive N-methylations of the same product.

The synthesis of 4,4'-dipyridyl diacetate has been described by Dimroth (Berichte, 54, 1921, page 2934; Ibid., 55, 1922, page 3,695). That method comprises the following steps:

(1) reducing pyridine with zinc and acetic anhydride to N,N'-diacetyl-tetrahydrodipyridyl:

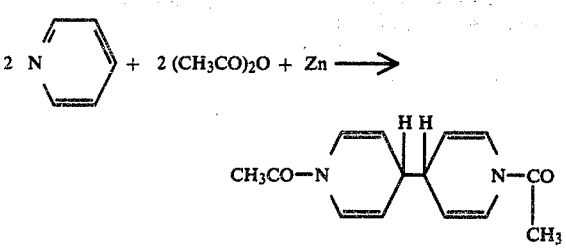

+(CH$_3$COO)$_2$Zn; followed by (2) oxidizing the N,N'-diacetyl-tetrahydrodipyridyl with oxygen, in a solvent, to dipyridyl diacetate:

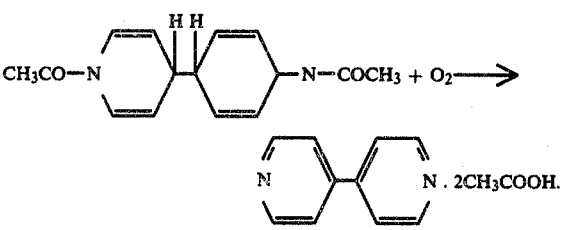

According to the cited author, when the diacetate (a colorless crystalline product, melting point=96° C.) is treated, in an aqueous medium, with ammonium hydrate, ammonium acetate forms and the base is liberated as 4,4'-dipyridyl dihydrate (melting point=73° C.) cyrstallizing to filiform needles.

To carry out the quaternarization of the latter substance, it was then necessary to dehydrate the 4,4'-dipyridyl dihydrate to 4,4'-dipyridyl (melting point=112° C.) and to treat it with methyl halide in a suitable solvent; or, according to French Pat. No. 1,390,773 of I.C.I., the quaternarization can be conducted in water.

It has now been found, and this is the object of the present invention, that N,N'-dimethyl dipyridylium dihalide can be directly prepared from dipyridyl diacetate, obtained through oxidation of diacetyl-tetrahydrodipyridyl, by treatment in an acetic acid solution with an alkyl halide in an autoclave under a pressure of 2–10 kg/cm$^2$, and at temperatures ranging from 50° to 150° C.

Suitable alkyl halides include lower alkyl halides such as methyl and ethyl chlorides, bromides and iodides. Methyl chloride is especially suitable.

The amount of acetic acid should be at least equal to that of the dipyridyl diacetate to be quaternarized.

Under these conditions, the yield is higher than 95% referred to the starting dipyridyl diacetate, the product has a purity of 98–99% and the acetic acid employed can be repeatedly recycled at both the oxidation and the quaternarization stage. It has been ascertained that the acetic acid can be recycled for more than 15 times without any decrease in the product purity or yields.

The use of acetic acid as solvent, besides securing a proper adjustment of the reaction exothermy and a uniform degree of quaternarization of the dipyridyl diacetate in every point throughout the reacting mass, permits one to avoid problems of separation or recovery of the acetic acid that is liberated during the reaction (representing 43.5% of the product subjected to reaction), because it mixes with the acetic acid employed as the solvent medium.

The following detailed examples are given still better to illustrate the invention:

EXAMPLE 1

825 g (2.86 moles) of dipyridyl diacetate (96% purity) prepared according to the conventional Dimroth reaction referred to above, were charged into an enameled 3.5-liter autoclave. 99% acetic acid (1635 g) were added thereto and the whole was heated to 114° C., beginning then to introduce methyl chloride at a pressure of 5.8 kg/cm$^2$.

The reaction was continued for 2 hours, whereupon the feeding of methyl chloride was stopped, while the heating, conversely, was continued for a further 2 hours.

After cooling, a slurry was obtained that was separated by filtration from wet crystals (1182 g), which were dried, while the acetic acid, separated by filtration, was utilized for further quaternarizations.

There were thus obtained 660 g of N,N'-dimethyl-4,4'-dipyridylium dichloride (90% calculated on the dipyridyl diacetate introduced) having a purity higher than 98%.

EXAMPLE 2

Into a 3.5-liter reactor there were charged 865 g (3.54 moles) of N,N'-diacetyl-tetrahydrodipyridyl (yellow crystals having a melting point of 132.5° C.) in 1700 g of recycled acetic acid containing dipyridyl diacetate at its solubility limit.

The mixture was heated to 40° C., and which temperature oxygen, finely dispersed in the reacting mass, began to be introduced, the reaction exothermy being moderated by cooling liquid circulating in the jacket of the reactor in order not to exceed a temperature of 50° C. in the inside.

The reaction was concluded in 1 hour. A brown solution was obtained that, by cooling, separated dipyridyl diacetate in crystals, which were recovered by filtration and dried.

800–820 g (2.86 moles) of dipyridyl diacetate (melting point=96° C.) were thus obtained, the yield being 76–80% calculated on the N,N'-diacetyl-tetrahydrodipyridyl. Acetic acid was recycled to the oxidizing reaction.

The resulting dipyridyl diacetate was quaternarized under the conditions of Example 1, but using as a solvent acetic acid coming from a preceding quaternarization.

720 g of N,N'-dimethyl-4,4'-dipyridylium dichloride at a purity higher than 98% were obtained.

EXAMPLE 3

The acetic acid suspension of dipyridyl diacetate, obtained under the conditions of Example 2, was directly charged, at a temperature of 50° C. and under stirring, to the enameled autoclave, where it was treated with methyl chloride (at 114° C. and 5.8 kg/cm$^2$), as described above in Example 1.

720 g of N,N'-dimethyl-4,4'-dipyridylium dichloride at a purity higher than 98% were thus obtained.

What is claimed is:

1. A process for quaternarizing 4,4'-dipyridyl diacetate to N,N'-dimethyl-4,4'-dipyridylium dihalide by reaction with an alkyl halide, characterized in that the reaction is conducted by:

using acetic acid as solvent for the dipyridyl diacetate in amounts of at least 1:1 by weight in respect of the diacetate subjected to reaction; and heating the reactants at temperatures ranging from 60° to 150° C. and at pressures ranging from 2–10 kg/cm$^2$.

2. A quarternarization process according to claim 1, wherein the acetic acid used as a solvent is utilized for further quaternarizations of dipyridyl diacetate.

3. A process according to claim 1 wherein the acetic acid used as a solvent in preparing N,N'-dimethyl-4,4'-dipyridylium dihalide is recycled to a stage wherein oxidation to form the 4,4'-dipyridyl diacetate occurs, and the resulting 4,4'-dipyridl diacetate is quaternarized as described in claim 1 in the same recycled acid.

4. A process according to claim 1, wherein the alkyl halide is methyl chloride.

5. A process according to claim 2, wherein the alkyl halide is methyl chloride.

6. A process according to claim 3, wherein the alkyl halide is methyl chloride.

* * * * *